(12) United States Patent
Hockman et al.

(10) Patent No.: US 7,946,588 B1
(45) Date of Patent: May 24, 2011

(54) TARGET RETRIEVAL SYSTEM

(76) Inventors: James Glen Hockman, Hedgesville, WV (US); Cletus Paul Hockman, Shepherdstown, WV (US)

( * ) Notice: Subject to any disclaimer, the term of this patent is extended or adjusted under 35 U.S.C. 154(b) by 0 days.

(21) Appl. No.: 12/659,315

(22) Filed: Mar. 4, 2010

(51) Int. Cl.
*F41J 7/02* (2006.01)
(52) U.S. Cl. ......................................... 273/406; 273/407
(58) Field of Classification Search .................. 273/359, 273/366–370, 403–410
See application file for complete search history.

(56) References Cited

U.S. PATENT DOCUMENTS

| | | | | |
|---|---|---|---|---|
| 1,075,518 A * | 10/1913 | Thresher | | 273/359 |
| 1,727,272 A * | 9/1929 | Caswell | | 273/406 |
| 2,290,297 A * | 7/1942 | Smith | | 273/370 |
| 2,344,829 A * | 3/1944 | McAvoy | | 104/173.1 |
| 2,494,210 A * | 1/1950 | Robinson | | 273/369 |
| 2,703,240 A * | 3/1955 | Flory | | 273/370 |
| 2,793,038 A * | 5/1957 | Wallace et al. | | 273/369 |
| 2,838,309 A * | 6/1958 | Merz et al. | | 273/406 |
| 3,020,047 A * | 2/1962 | Spieth | | 273/406 |
| 3,363,900 A * | 1/1968 | Cadle | | 273/359 |
| 3,471,153 A * | 10/1969 | Baumler | | 273/359 |
| 4,072,313 A * | 2/1978 | Murso et al. | | 273/359 |
| 4,081,056 A * | 3/1978 | Siitonen | | 185/6 |
| 4,286,788 A * | 9/1981 | Simington et al. | | 273/359 |
| 4,890,847 A * | 1/1990 | Cartee et al. | | 273/406 |
| 5,367,232 A | 11/1994 | Netherton et al. | | |
| 5,368,307 A | 11/1994 | Hotchkiss | | |
| 5,577,734 A * | 11/1996 | Conroy | | 273/407 |
| 6,257,584 B1 | 7/2001 | Nasuti | | |
| 7,614,626 B1 * | 11/2009 | Aanerud et al. | | 273/367 |
| 2007/0029733 A1 * | 2/2007 | Anderson, Jr. | | 273/408 |
| 2008/0088089 A1 * | 4/2008 | Bliehall et al. | | 273/359 |
| 2008/0207357 A1 * | 8/2008 | Savarese et al. | | 473/407 |

* cited by examiner

*Primary Examiner* — Mark S Graham

(57) ABSTRACT

A practice ground for a bow and arrow hunter which allows the hunter selectively to position the target at various locations from a shooting area, to shoot arrows thereat, to retrieve the targets to ascertain the results, and to retrieve the arrows in the target, all without leaving the shooting area. The practice ground has a stand built into a tree simulating a field-type shooting area, a target, a target supporting tow line, and a plurality of stanchions with pulleys supporting and guiding the tow line. The tree stand includes a manual drive mechanism for moving the target to and from the hunter.

11 Claims, 13 Drawing Sheets

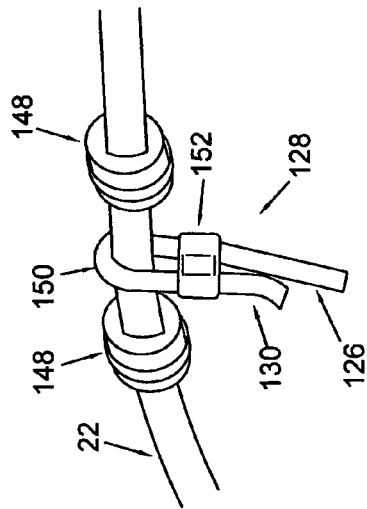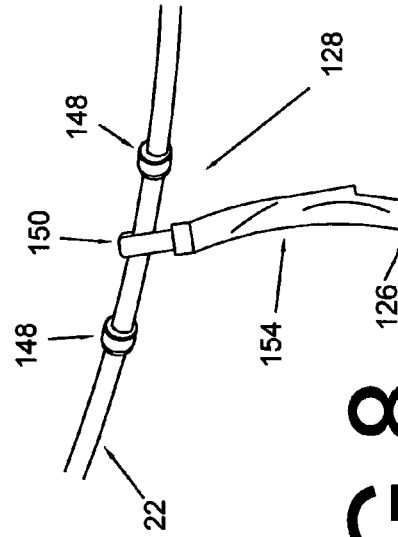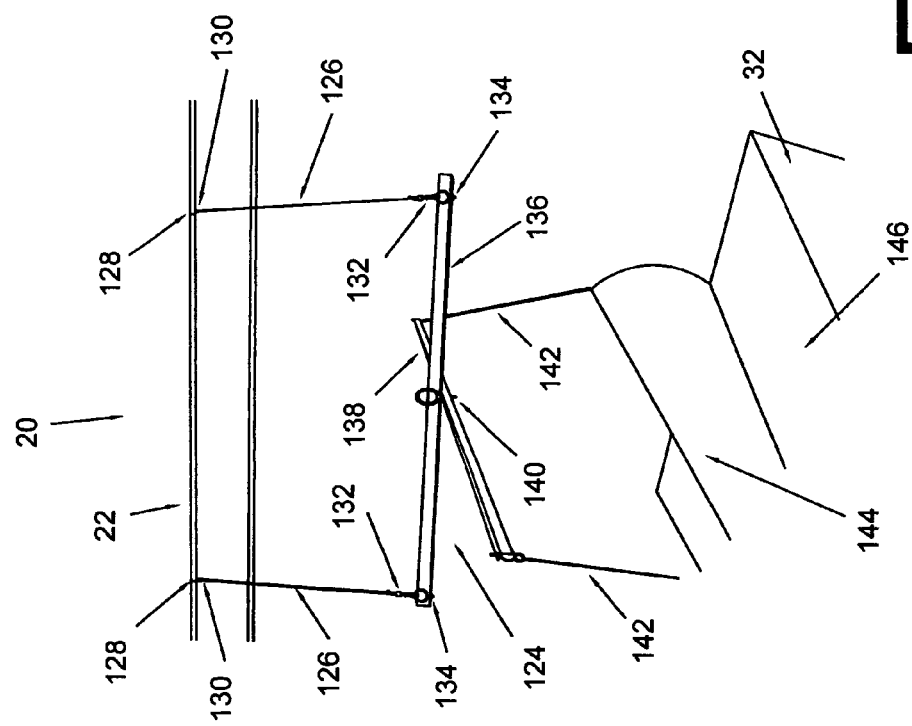

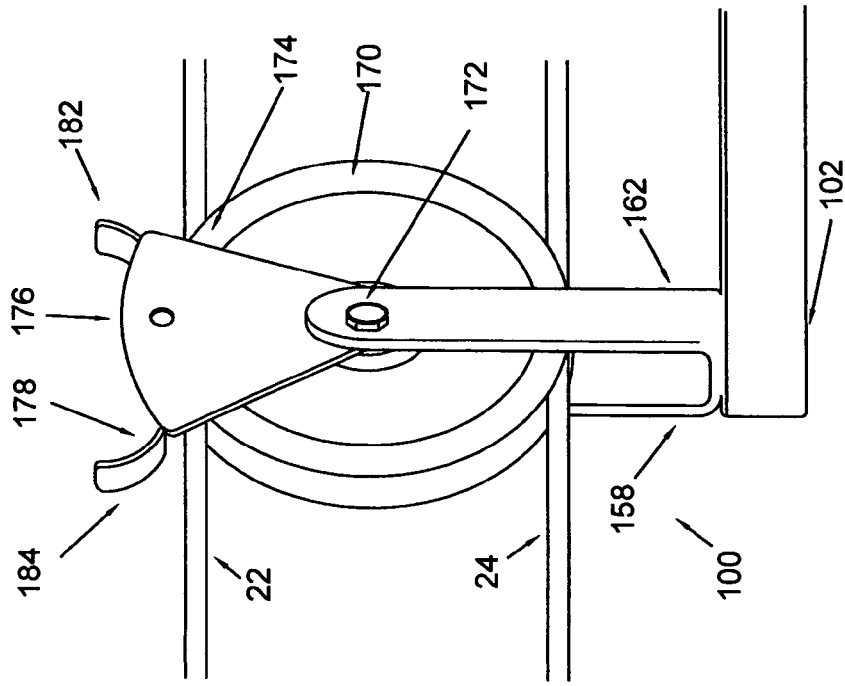
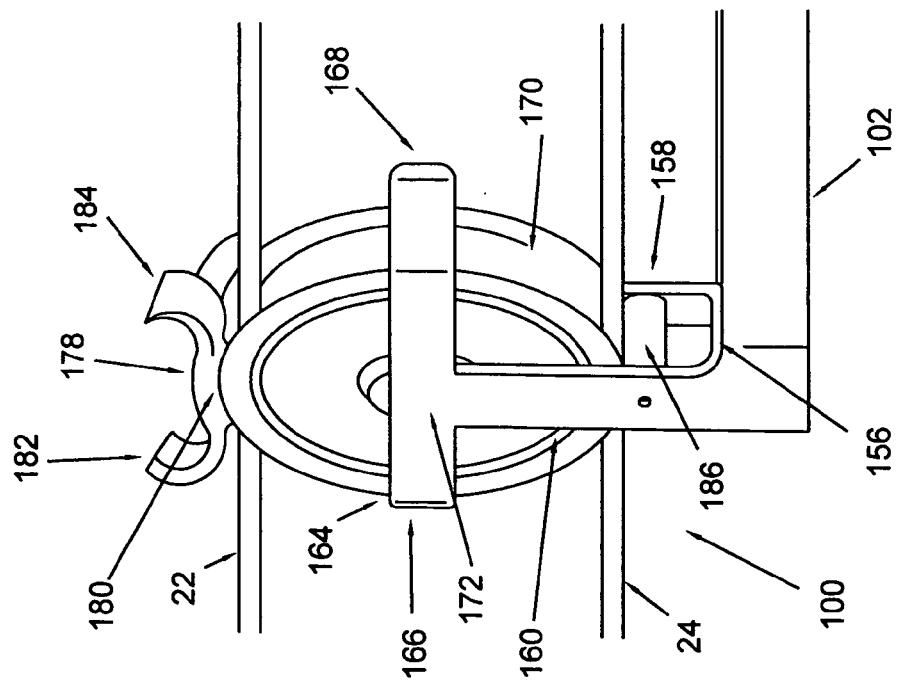

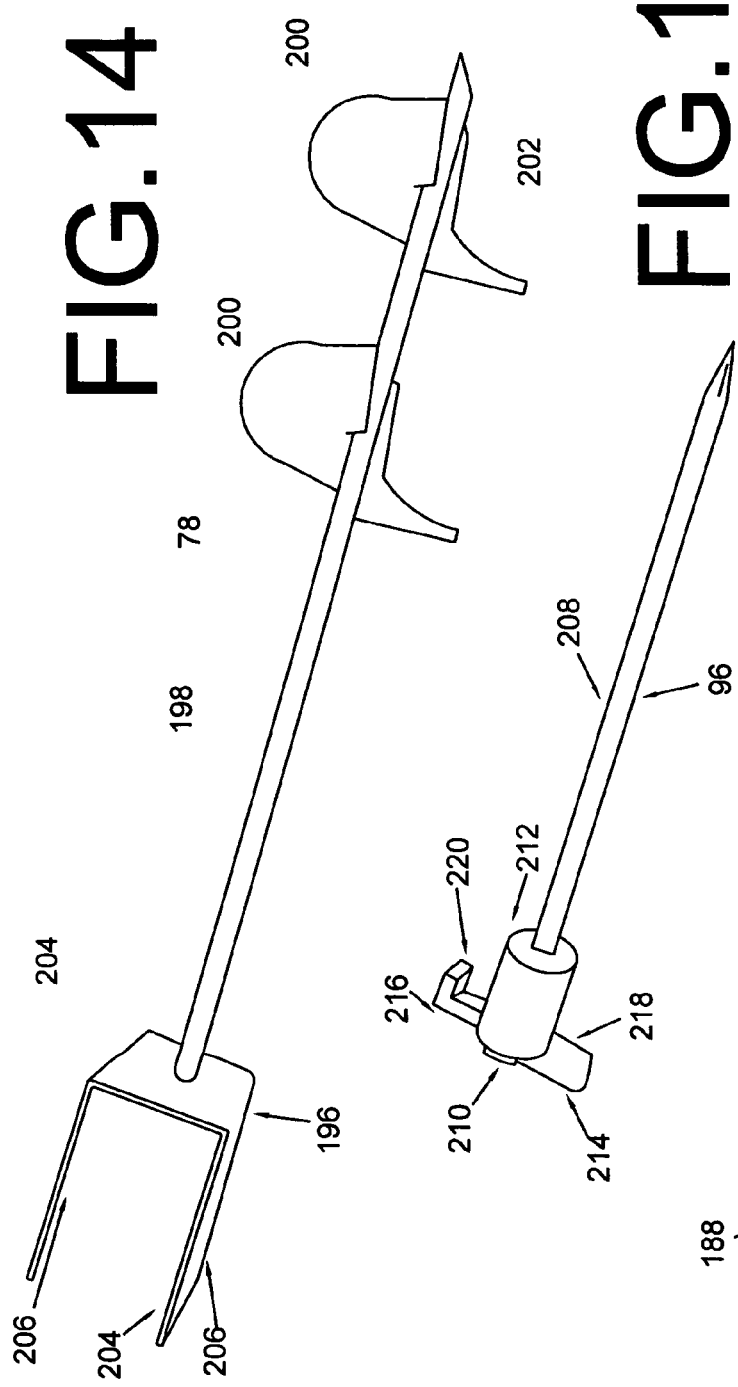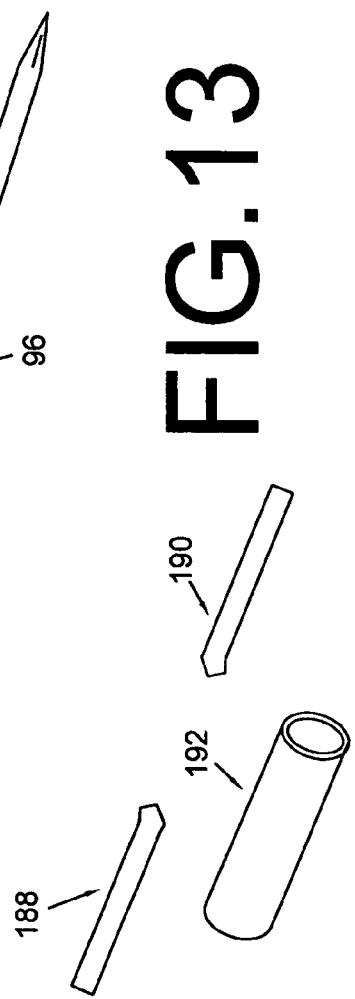

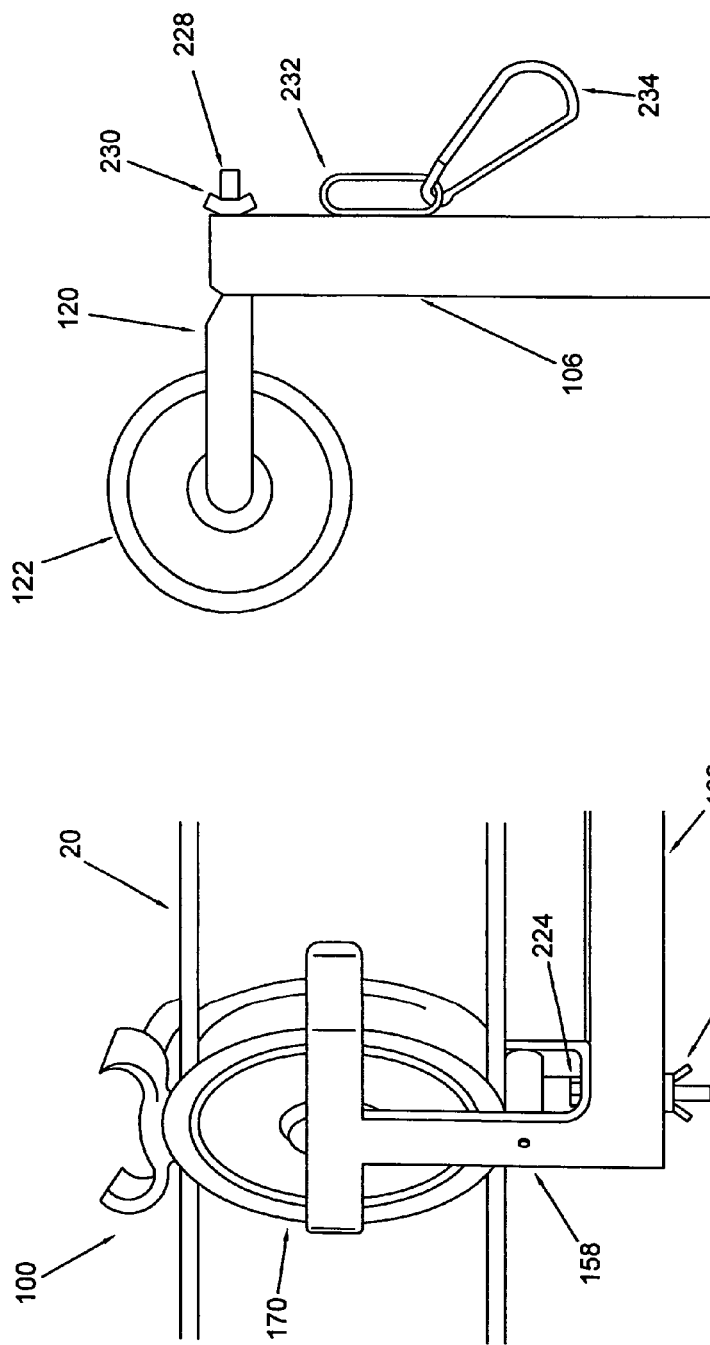

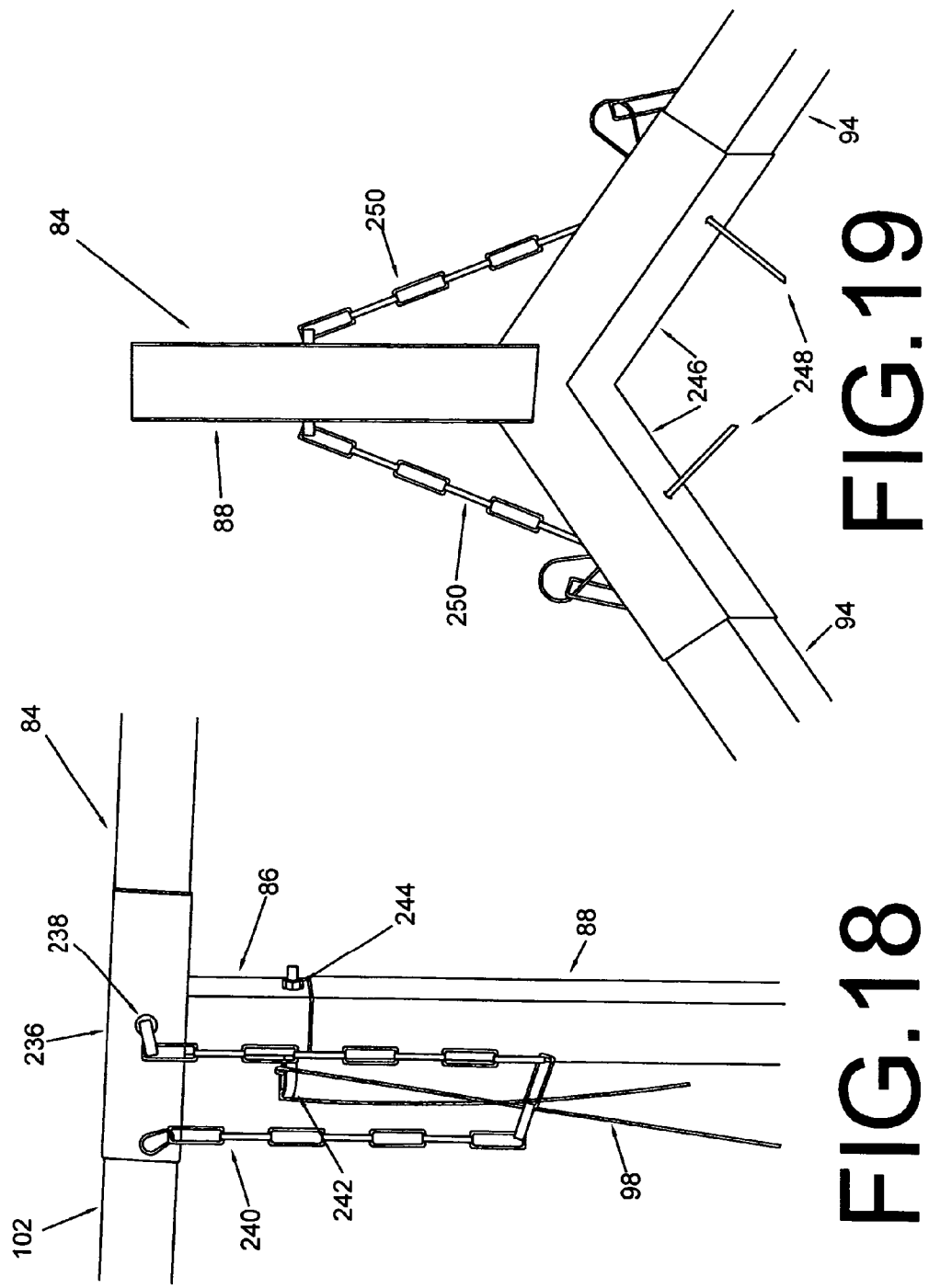

TARGET RETRIEVAL SYSTEM

BACKGROUND OF THE INVENTION (1) Field of the Invention

This invention relates to a practice system for a bow and arrow hunter which allows the hunter selectively to position the target at various locations from a shooting area, to shoot arrows thereat, to retrieve the targets to ascertain the results, and to retrieve the arrows in the target, all without leaving the shooting area.

(2) Description of Related Art Including Information Disclosed Under 37 CFR 1.97 and 1.98

The references of record are a good representatitive of the state of the art. The only patent of which the inventors are aware which relates in any way to the invention is U.S. Pat. No. 5,367,232, issued to Netherton et al. on Nov. 22, 1994. Netherton et al. show an archery hunter's practice setup in which a drive pulley and a plurality of idler pulleys are attached to trees. A cable loop is driven by a motor associated with the drive pulley to move one or more targets hung from the cable around the pulley-defined path, thus simulating the movement of an animal in the woods, allowing practice at shooting at a moving target. The differences are too numerous to mention them all. To set forth a few: One, the arrows that miss the target are sprayed in Netherton et al. around the closed path; in the instant invention, those arrows that are not in the target itself, are grouped near the selectively fixed location of the target. Two, the target moves "on its own," so to speak; it moves continuously or it is not in use. The hunter of Netherton et al. either turns it on or turns it off; in the instant invention, the hunter controls the movement and location of the target at all times. And, three, Netherton et al. need outside structures, tree, buildings, etc.; in the instant invention, a series of pulley stanchions are carried to the practice ground, including at least a tension station, a drive station, an intermediate station, and an end station, in order to set up the shooting course without need of outside equipment or structures. Numerous other differences, each of which negate anticipation, also exist.

BRIEF SUMMARY OF THE INVENTION

The disclosed invention satisfies the needs of hunters or target shooters of all kinds by providing a shooting ground comprising a target, a shooter's stand, and a target retrieval system between the two. The target retrieval system comprises a closed loop of cable with the target attached thereto, and a drive pulley (1) for moving the target to a desired location away from a shooting stand for practice shooting thereat, and (2) for retrieving arrows hitting the target by selectively moving the target from its desired location back to the shooting stand.

BRIEF DESCRIPTION OF THE DRAWINGS

The foregoing and other objects, aspects, uses, and advantages of the present invention will be more fully appreciated as the same becomes better understood from the following detailed description of the present invention when viewed in conjunction with the accompanying drawings:

FIG. 6 is a diagrammatic perspective view of the target support assembly;

FIGS. 7-8 are enlarged perspective views of the connection between the target support assembly and the tow line;

FIG. 9 is a diagrammatic front perspective view of the intermediate support station pulley wheel;

FIG. 10 is a diagrammatic rear perspective view of the intermediate support station pulley wheel;

FIG. 13 is an exploded perspective view of a preferred cable splice;

FIG. 14 is a diagrammatic perspective view of a preferred anchor;

FIG. 15 is a diagrammatic perspective view of a stake;

FIG. 16 is a diagrammatic perspective view of a preferred alternative of the mounting of the intermediate support station pulley wheel;

FIG. 17 is a diagrammatic perspective view of a preferred alternative of the mounting of the end station pulley wheel;

FIG. 18 is a diagrammatic perspective view showing the attachment of the top horizontal bar to the stanchion of the intermediate support station;

FIG. 19 is a diagrammatic perspective view showing the attachment of the base to the stanchion of the intermediate support station;

DETAILED DESCRIPTION OF THE INVENTION

The description is in view of an archery hunter practice-shooting his bow and arrow from an elevated tree stand at a target temporarily stationed at various distances. From his single purchase, the hunter may position the target, shoot his arrows thereat, withdraw the target to his elevated position, retrieve the arrows, inspect the target, and reposition the target at the same or a different distance for further practice. It is readily apparent to one skilled in the art that any hunter could use the disclosed system to shoot any weapon at any target.

It is also readily apparent that the target retrieval system may be set up anywhere, e.g., in the back yard of a home or in a common field. The functional equivalent of the "tree stand" is a deck, a corner of the yard, or any other place which a user might find convenient as a shooting area from which to loose his arrows. For example, a tree stand has been shown, but the drive pulley could as well be supported by another stanchion brought to the practice ground.

The description is intended to satisfy the requirements of the statute and is not intended to be all inclusive. In all of the figures, the invention is depicted to emphasize understanding thereof and is not necessarily to scale.

Figure 1:
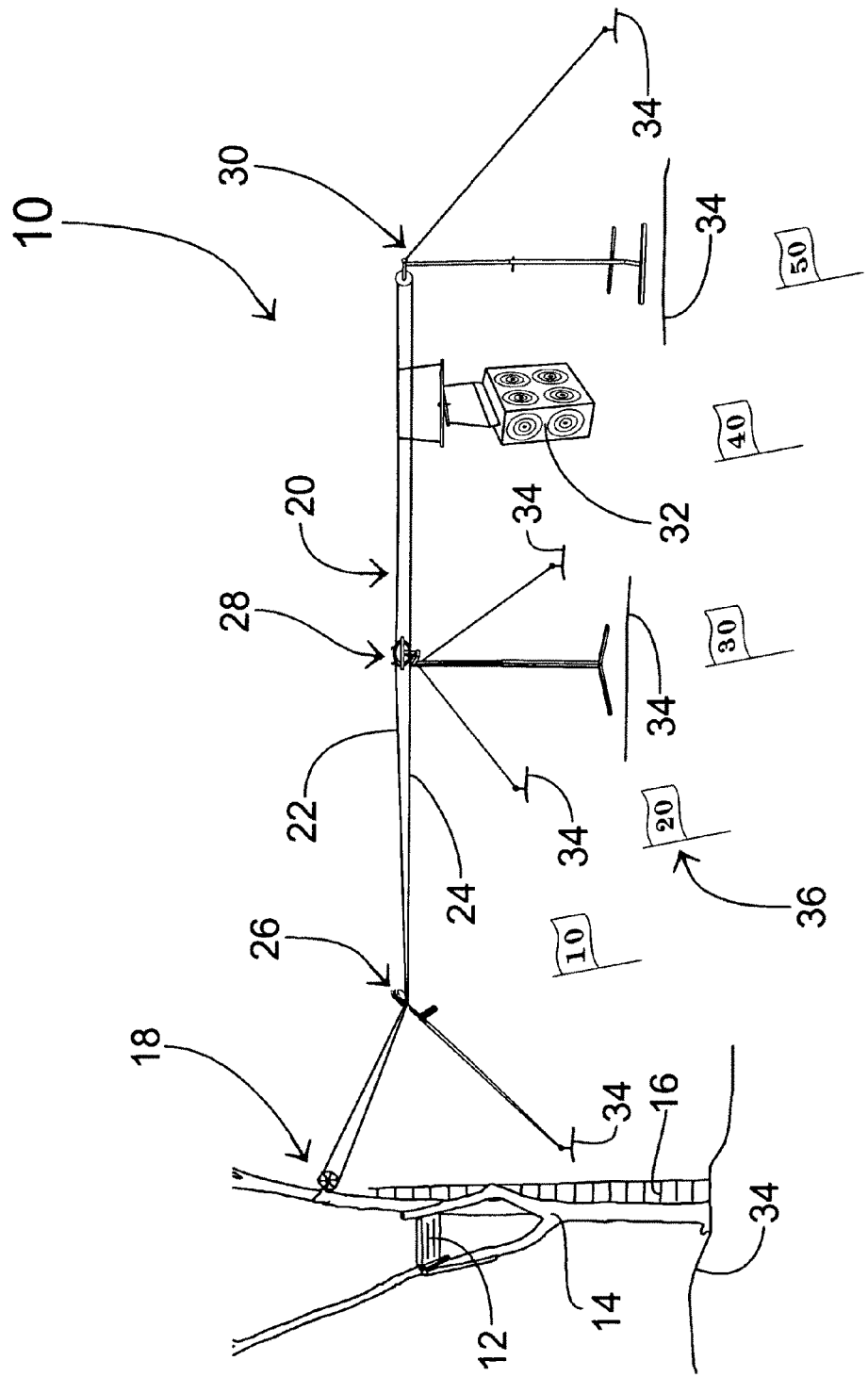
FIG. 1 is a diagrammatic showing of a target retrieval system showing the overall scheme of the invention.

Target retrieval system 10 is shown diagrammatically in FIG. 1.

A tree stand 12 is built in a tree 14, simulating a hunter's tree stand in the forest, and a ladder 16 provides access to tree stand 12. Tied to the trunk or a large branch of tree 14 is a drive 18 which moves a conveyor 20, preferably a tow line 20, back and forth throughout target retrieval system 10. Tow line 20 comprises a top rope 22 and a bottom rope 24. Inasmuch as the tow line material may vary, referring to it as a "line" and/or "rope" is generically descriptive. Tow line 20 is a continuous line whose free ends are joined together in the manner shown in FIGS. 7-8. As such, it is a closed entity whose length is preselected by the hunter, the user, the seller, or the purchaser of system 10. From drive 18, tow line 20 passes through tension adjusting station 26, at least one intermediate support station 28, and an end station 30. A target 32 is suspended from top rope 22 and is movable back and forth between drive 18 and end station 30. All components, including the tree 14 are supported ultimately by the ground 34.

A plurality of flags 36 are provided. Each flag 36 has a distance numeral thereon, signifying the yardage from the tree stand 12 to the staked location. The flags 36 are shown as from ten to fifty yards. They would of course reflect suitable amounts. The distance is determined to each selected point of the target retrieval system 10 by conventional means, e.g., range finders, paced off, etc., and a flag is grounded. The distances need not be totally accurate, but of course the more accurate they are, the more helpful is the practice.

Figure 2:
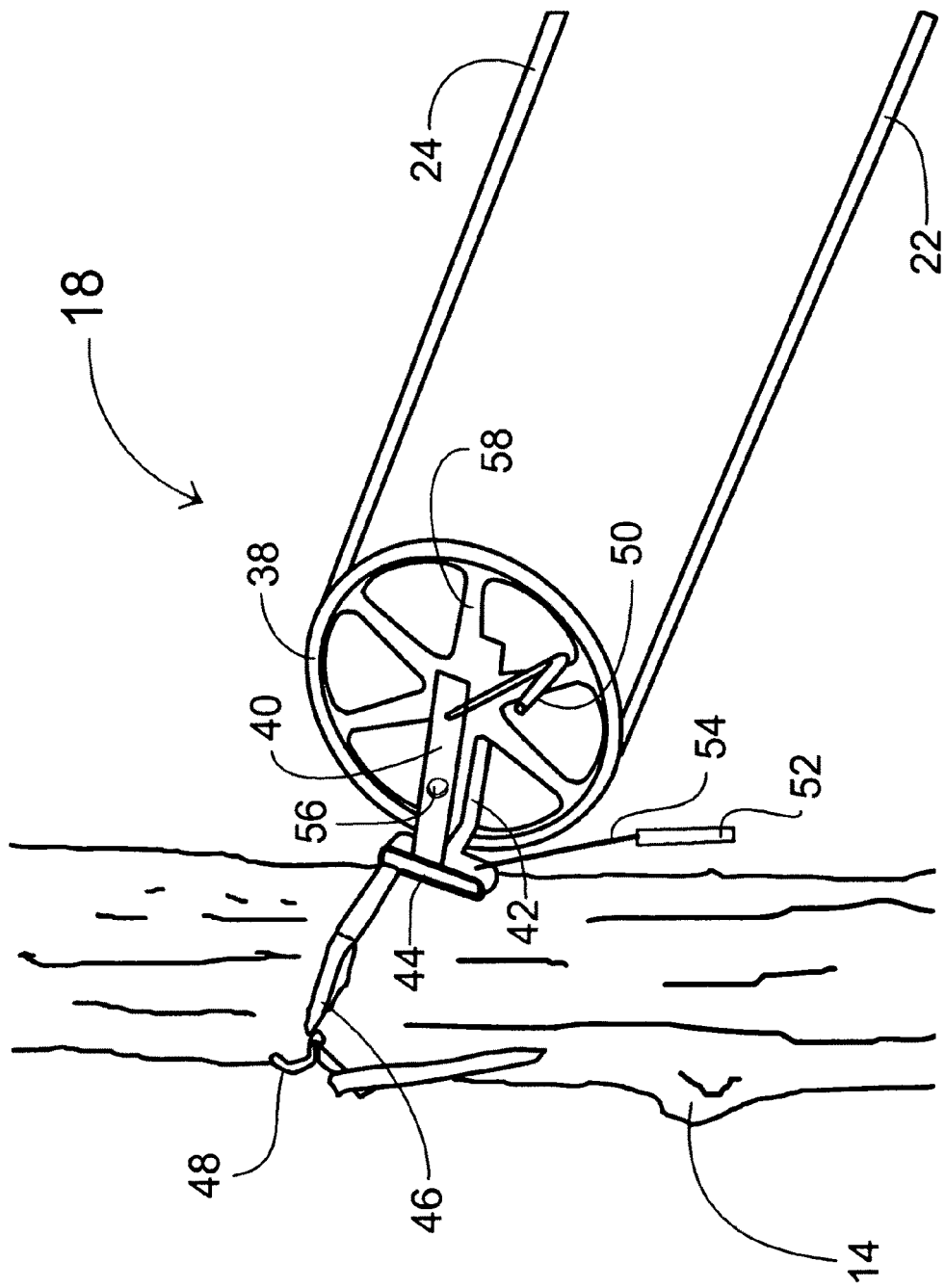
FIG. 2 is a diagrammatic perspective view of the drive pulley and associated elements.

Drive 18 is more clearly shown in FIG. 2. A drive pulley wheel 38 is journaled between the two bracket arms 40 and 42 of a bracket 44 which is tied to tree 14 by a strap 46. A U-shaped staple 48 driven into tree 14 prevents strap 46 from sliding down tree 14. A hand crank 50 rotates drive pulley wheel 38 to position target 32 at a desired location and to retrieve it as needed. It has been found that a rubber band (not shown) which is wrapped around pulley 38 in its sheave adds friction between pulley 38 and tow line 20 which aids in smoothly moving target 32 to and from drive station 18. An electrical motor powered by batteries or an adapter may also be used to drive pulley 38.

When target 32 is withdrawn to a position adjacent drive pulley wheel 38, it is on a downwardly sloping top rope 22 (the relative reversal of position of top rope 22 will be explained soon). Gravity continuously acts on target 32 causing it to move downwardly away from drive 18, thus rotating all of the pulleys simultaneously. In order to keep target 32 stationary after retrieval, a pin 52, affixed to bracket 44 by a tether 54, is inserted through a pair of aligned apertures 56 (only one shown) through both bracket arms 40 and 42 of bracket 44. Pin 52 passes between the spokes 58 of drive pulley wheel 38. As pulley wheel 38 is rotated by a moving target 32, a spoke 58 abuts pin 52, stopping the rotation of wheel 38, and thereby constraining drive 18 and, in turn, target 32 in place. Pin 52 may be used to fix target 32 in any selected location.

Figure 3:
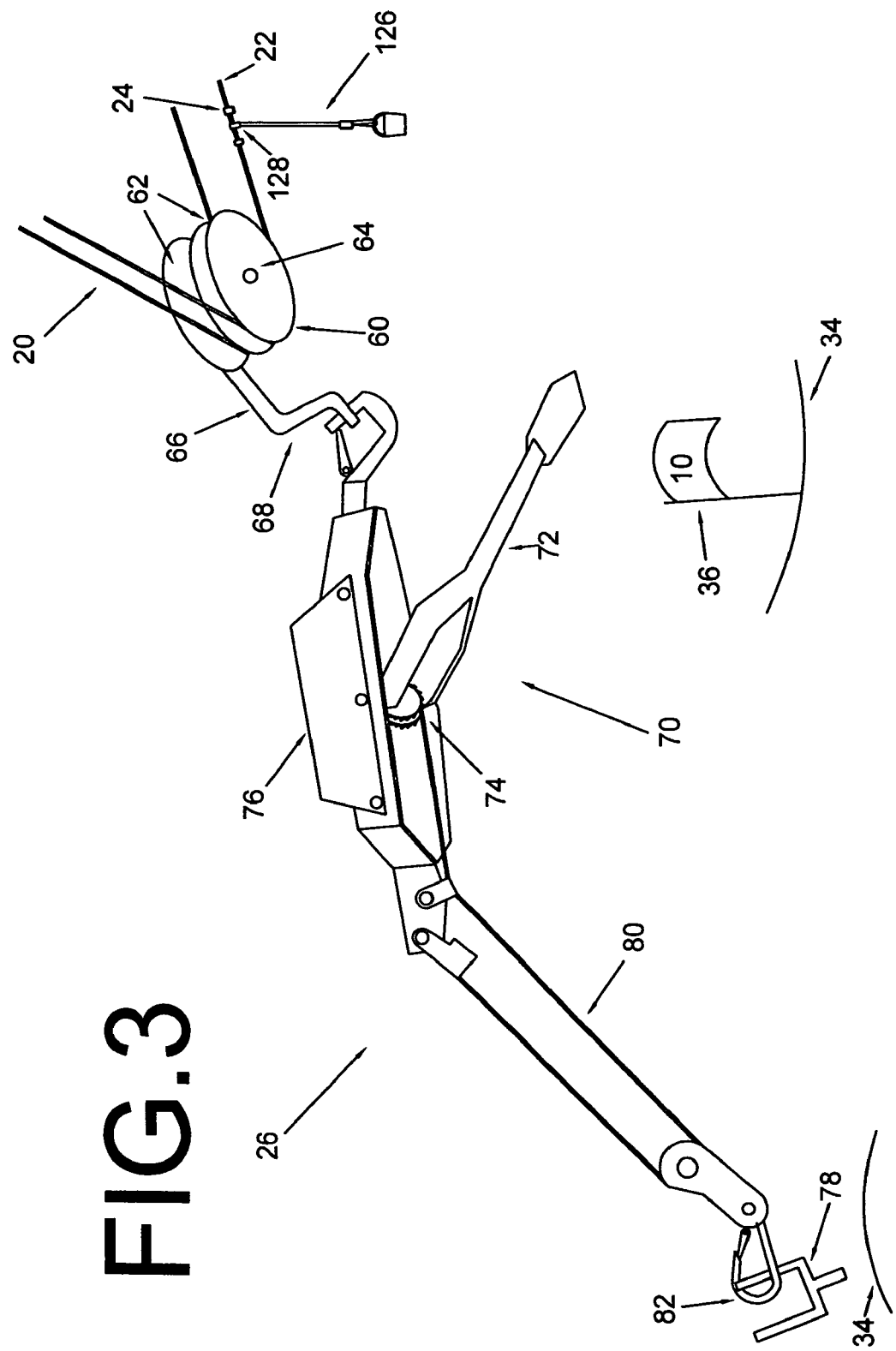
FIG. 3 is a diagrammatic perspective view of the tension adjusting station.

FIG. 3 shows adjusting station 26 as a free-standing assemblage whose central feature is a tension adjusting pulley 60. Pulley 60 is shown as a single pulley which has two parallel sheaves 62 with a single axis 64. A pair of single pulleys, each with a single groove, fixed together and journaled on the same axis, would do as well. Pulley 60 is journaled on the single arm 66 of a bracket 68 and receives top and bottom tow ropes 22 and 24 of tow line 20 in its two sheaves. The relative position of top and bottom tow ropes 22 and 24, respectively, are reversed when passing around pulley wheel 60 as will be discussed later.

Tension is maintained in tow line 20 by a commercially available tension adjuster 70. Manual cranking of handle 72 ratchets a toothed drum 74 rotatable in housing 76 of tension adjuster 70. The tension between bracket 68 and cork-screw anchor 78 is adjusted by means of an extensible cable 80. A hook 82, a part of tension adjuster 70, is diagrammatically shown as removably attached to cork-screw anchor 78. The tension of cable 80 as manually adjusted by tension adjuster 70 finds an immediate positive response in the tension of tow line 20.

Figure 4:
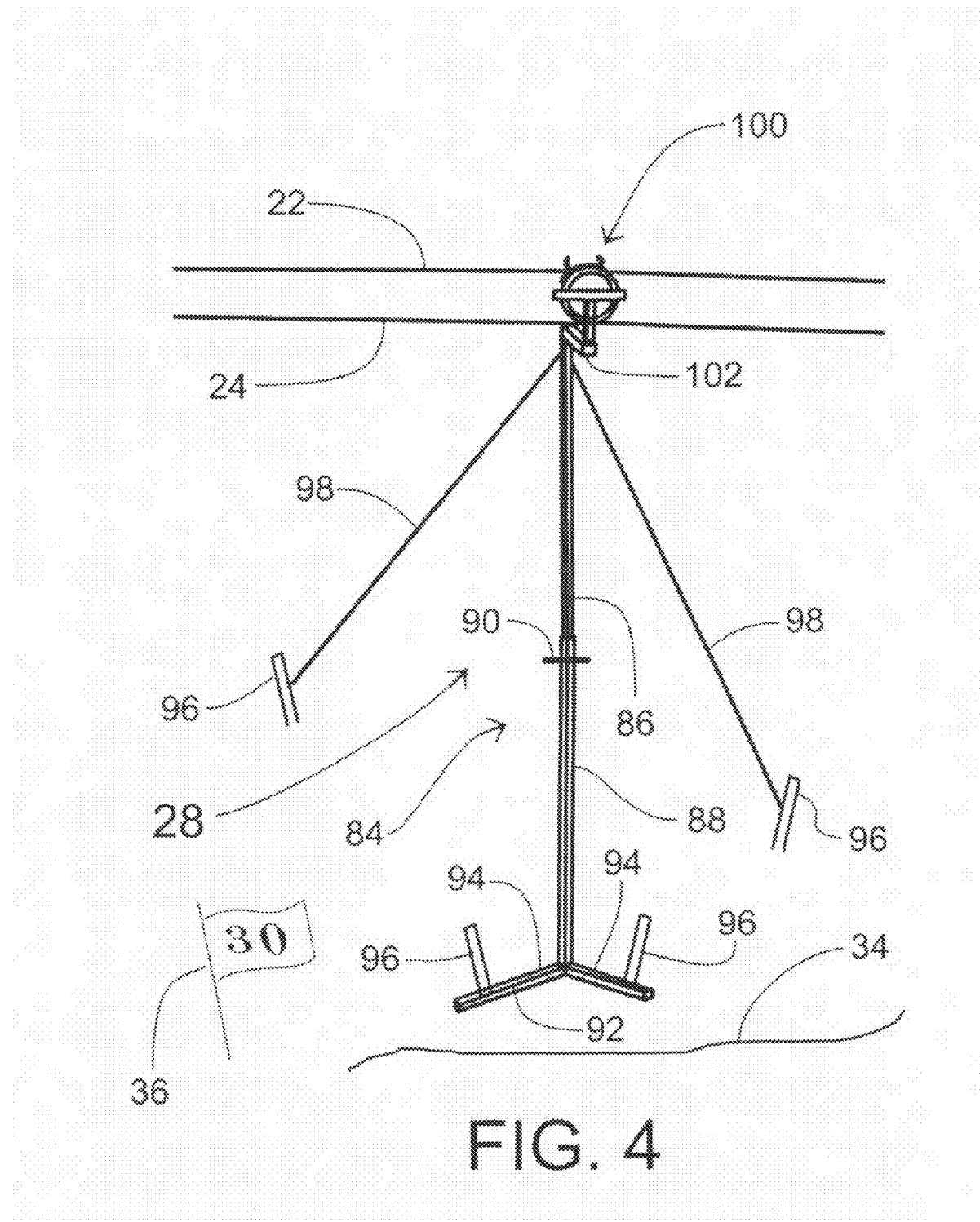
FIG. 4 is a diagrammatic perspective view of an intermediate support station.

FIG. 4 shows a front view of intermediate station 28. A telescopically adjustable stanchion 84 has two interleaving top and bottom poles 86 and 88, respectively. Pole 86 slides within pole 88, and a pin 90, inserted through aligned apertures in both poles 86 and 88, holds stanchion 84 together and stationary. A plurality of apertures through both interleaving poles 86 and 88 permits the user to selectively adjust the height of stanchion 84. Bottom pole 88 rests on a base 92 standing on ground 34. A pair of legs 94 extend away from the bottom end of bottom pole 88 to support stanchion 84. Legs 94 form an angle therebetween of approximately ninety degrees. Each leg 94 of base 92 has at least one pair of vertically aligned apertures formed therethrough, and a stake 96 is inserted through said base apertures and is driven into the ground 34 to anchor and stabilize stanchion 84. As many guy wires 98 as are deemed necessary are anchored between stanchion 84 and ground 34 by stakes 96. The term "guy wire" denotes any flexible entity which stabilizes the stanchion and is not necessarily a wire per se. A four point anchoring system has been found sufficient to efficiently support intermediate station 28. A pulley assembly 100 rests atop stanchion 84 and passively guides a top rope 22 and a bottom rope 24. Pulley assembly 100 is cantilevered from the top of stanchion 82 by a horizontal bar 102. A distance flag 36 is shown near support station 28.

The target retrieval system 10 is shown as on a substantially level ground. This is for convenience only. An uneven surface can be accommodated as well. System 10 is adapted to the undulations by locating support stations 28 and end station 30 appropriately and by adjusting the dimensions of the necessary station stanchions. Target 32 is thereby maintained out of contact with the ground 34.

Any number of support stations 28 between adjusting station 26 and end station 30 may be used, depending upon the topological features and how long the target retrieval system 10 is intended to be.

Figure 5:
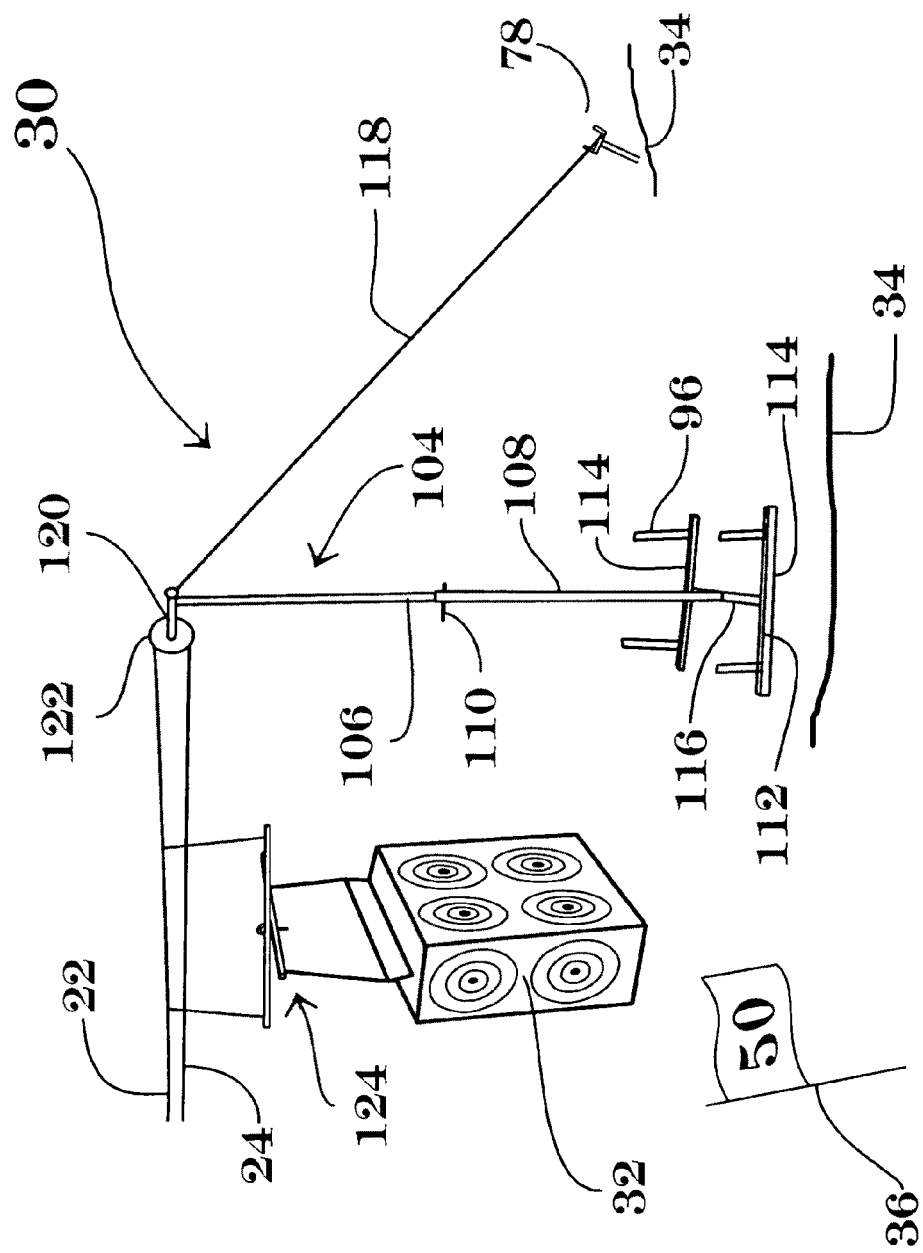
FIG. 5 is a diagrammatic perspective view of the end station.

End station 30 is shown in FIG. 5. A stanchion 104 comprises an interleaved pair of top and bottom poles 106 and 108, respectively, in the manner of stanchion 84 in FIG. 4. The height of stanchion 104 is selectively fixed by a pin 110. Stanchion 104 is supported on a base 112 on the earth 34. Base 112 comprises three feet, two parallel feet 114 pointing toward intermediate station 28 and a cross-foot 116 connecting the two feet 114.

Base 112 is a larger base than base 90, inasmuch as base 112 is at the end of target retrieval system 10 and is under more tension than support station 28. Each of the feet 114 of base 112 preferably has a pair of vertical, aligned apertures therethrough near its end, and a stake 96 is driven through each pair of apertures into ground 34 in order to stabilize stanchion 104. Stakes are not strictly necessary, so their use is optional. The main resistance to the tension of the entire target retrieval system 10 is absorbed by a chain 118 attached to a cork-screw anchor 78 buried in the ground 34. Functionally, chain 118 is a guy wire for stanchion 104.

Drive station 18 and stations 26 and 30 bear the brunt of the tensions present in target retrieval system 10. In order to counteract the increased tensions, the increased strength of cork-screw anchor 78 over stakes 96 is needed relative to only two stations, tension adjusting station 26 and end station 30. If drive station 18 is a stanchion, stanchion 104 is a good candidate, and anchor 78 is preferred to stake 96.

A horizontally oriented, U-shaped bracket 120 is welded to the top of top pole 106 and has an end pulley 122 journaled therein. A preferred alternative to fixing U-shaped bracket 120 and top pole 106 is shown in FIG. 16. Top and bottom ropes 22 and 24 wrap around end pulley 122 and reverse direction thereat. A flag 36 is inserted into the ground 34 to mark the approximate yardage from tree stand 12.

A suspension assembly 124 allows target 32 to be suspended from top rope 22 and arranged in any universal position relative to tree stand 12. An enlarged depiction of assembly 124 follows in FIG. 6.

The universal suspension assembly 124 for target 32 is shown in FIG. 6 suspended from top rope 22. Each suspension wire 126 is loosely attached 128 at its top end 130 to top rope 22. A rotatable clip 132 is secured at the bottom end of wire 126, and a combination eye bolt and wing nut 134 connects each clip 132 to an end of a target suspension bar 136. A hollow aluminum tube, three-quarter inch square, approximately thirty-six inches long, is a good choice for bar 136. It is light, strong, easily worked, and is readily available commercially. Gravity and the spaced-apart fixing of suspension wires 126 forces the alignment of target suspension bar 136 with tow line 20. In order to orient target 32 relative to the bow hunter using target retrieval system 10, a target orientation bar 138 is connected to suspension bar 136 at a selected angle by a second combination eye-bolt and wing nut 140. Suspension wires 142 connect the ends of bar 138 with a flexible flange 144 centrally oriented on the top 146 of target 32. Target orientation bar 138 is also a hollow aluminum tube, three-quarter inch square, whose length can be selected based on the size of target 32.

Target 32 is shown in FIGS. 1 and 5-6 as a box-like structure made up of material which would stop and hold an arrow. A plurality of concentric circles are printed on the outside surface of the box as indicia for indicating the accuracy of the shooter. A simulated animal, such as a deer made of similar materials, would be a reasonable alternative, as it simulates shooting at an actual animal. Both are suspended from tow line 20 in the manner indicated.

The connection 128 of each suspension wire 126 and top rope 22 is shown in detail in FIGS. 7-8. A pair of split ferrules 148 are crimped onto top rope 22 about an inch apart. The free end 130 of wire 126 is bent around top rope 22 and back adjacent the body of wire 126 to form a loosely fitting loop 150. Another ferrule 152 is crimped onto the juxtaposition of free end 130 and wire 126. A piece of electrical tape 154 (FIG. 8) is applied to the lower part of ferrule 152, free end 130, and the body of wire 126 to cover the jagged wires of free end 130.

FIGS. 9 and 10 show the front and back perspective views of the intermediate support station 28.

In FIG. 9, horizontal bar 102 is cantilevered from stanchion 84 (not shown). Target 32 may therefore pass intermediate support station 28 beneath bar 102 without contacting it or stanchion 84, even when target 32 is canted relative to the line of travel of tow line 20. The bottom bight 156 of a U-shaped bracket 158 is welded to the end of bar 102. (See FIG. 16 for an alternative mounting.) The plane defined by both upright arms 160 and 162 (FIGS. 9 and 10, respectively) is aligned along the linear direction of bar 102 and perpendicular to tow line 20. Front arm 160 is substantially coincident with the end of bar 102 and faces upwardly away from bar 102. Attached at the top of arm 160 is a horizontal cross-piece 164 with a smooth outside surface. The ends 166 and 168 of cross-piece 164 are bent backwards beyond both edges of intermediate support pulley 170. Pulley 170 is journaled in the two upright arms 160 and 162 of U-shaped bracket 158 by a bolted axle 172.

It is preferred that cross-piece 164 be welded on its inside surface to the top of the head of axle 172, as this guarantees the smoothness of the outside surface of cross-piece 164. Also, axle 172 is easier to handle by means of cross-piece 164 than by a small head. It is likewise preferred to weld cross-piece 164 to the outside surface of top of arm 160, as this maintains the orientation of cross-piece 164 and arm 160. Both embodiments have their individual benefits which the user may choose, both result in the same configuration, and both are a part of the invention as a whole.

Turning to FIG. 10, rear arm 162 has a triangular-shaped plate 174 bolted to rear arm 162 by axle 172. Plate 174 is removable, in order that pulley 170 be removable as well in order to add tow line 20 to pulley assembly 100. The top edge 176 of triangular-shaped plate 174 is arched to match the curvature of pulley 170. Integral with plate 174 and coincident with a large part of the length of top edge 176 of plate 174 is an arched flange 178. The elongated extent of top edge 176 of plate 174 gives strength and stability to flange 178. Flange 178 is substantially horizontally cantilevered from top edge 176 and is located slightly above pulley 170 (FIG. 9), where it is spaced from the edge of pulley 170 a distance 180 slightly smaller than the diameter of top rope 22 but slightly larger than the diameter of suspension wire 126, i.e., between one-eighth inch and one-sixteenth inch. In those situations in which support station 28 is at a lower elevation than the surrounding stations, flange 178 will prevent top rope 22 from rising uncontrollably and leaving the top of pulley 170. Flange 178 has two upwardly curved ends 182 and 184 facing, respectively, the two directions of tow line 20 to smoothly wedge any upwardly riding top rope 22. Roller 186 (FIG. 9) is separately journaled in the two upright arms 160 and 162 of U-shaped bracket 158 in order to maintain bottom tow rope 24 within pulley 170 as well and to not allow it to sag under the force of gravity.

A particular problem is solved by this invention, namely, unimpeded movement of the target past the intermediate pulleys. In its travels from end station 30 to tree 14, target 32 must pass all of the intermediate pulleys without mutual interference between target 32 and any other part of target retrieval system 10. In order to do so, it must pass two different types of pulleys.

The manner in which target 32 bypasses tension adjusting station 26 is now described. Refer to FIG. 3 while reading the following. Because extensible cable 80 is pivotally connected to bracket 68, the plane of pulley 60 lies in the plane defined by tow line 20 extending in different directions on each side of pulley 60. There is a danger of suspension wires 126 becoming tangled with bracket 68 and/or pulley 60. A single-arm 66 for bracket 68 which lies over the top of pulley 60 sets the stage to eliminate this entanglement.

Reversing the relative position of top rope 22 and bottom rope 24 completes the solution. The top rope 22 being located at the bottom of pulley 60, a condition shown in FIG. 3, allows gravity to pull target 32 (not shown) below pulley 60 away from bracket 68. The connection 128 of suspension wires 126 comprising ferrules 148 and loop 150 rides through the lower sheave 62 of double-sheave pulley 60, causing suspension wires 126 to dangle freely over the edge of pulley wheel 60, out of conflict with any other parts of the target retrieval system 10. Not so with pulley 170 of intermediate support station 28.

Figure 12:
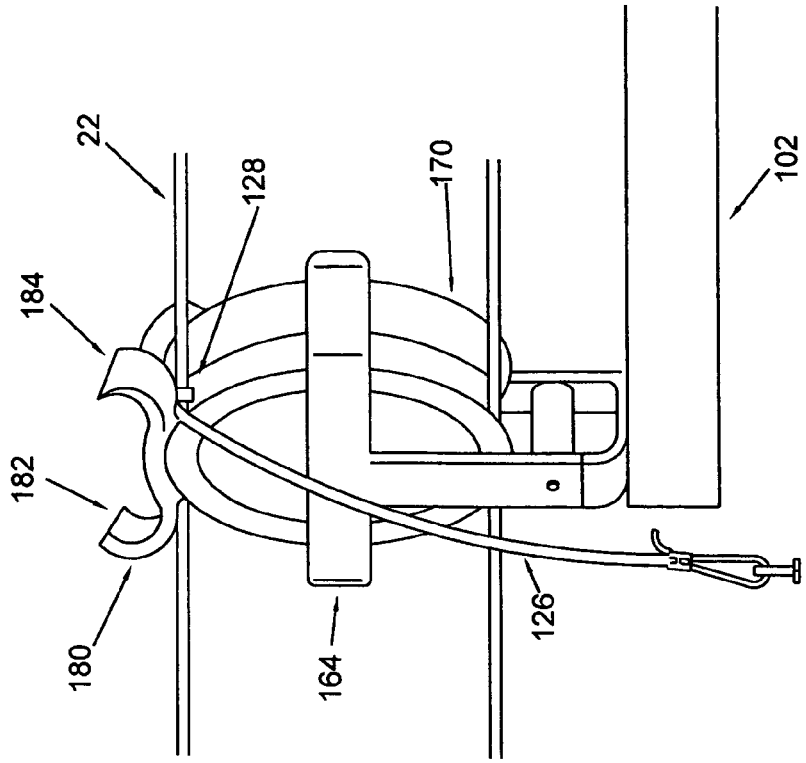
FIG. 12 is a diagrammatic front perspective view of the intermediate support station pulley wheel with a target suspension wire passed halfway.
Figure 11:
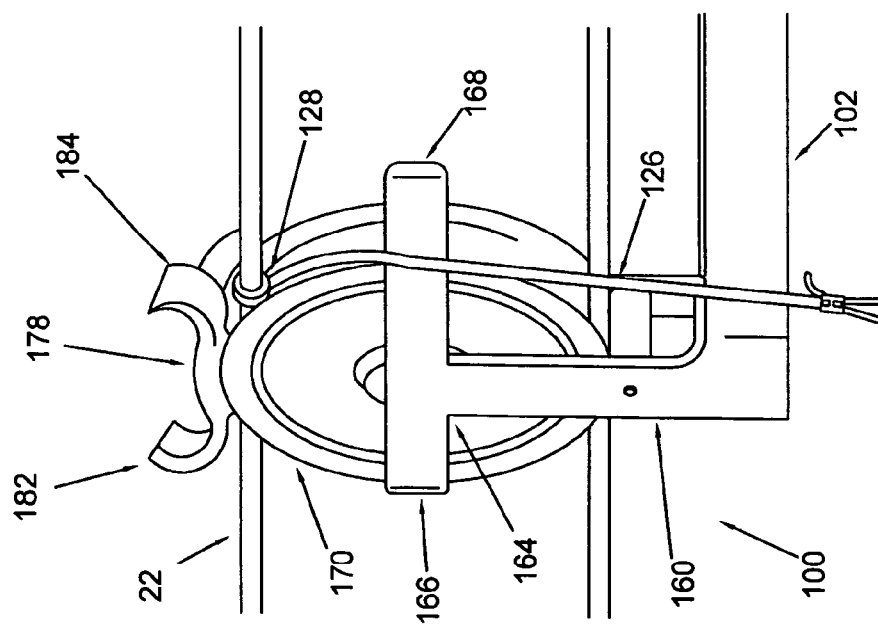
FIG. 11 is a diagrammatic front perspective view of the intermediate support station pulley wheel and a target suspension wire beginning to pass by it.

Referring to FIGS. 11 and 12, suspension wire 126 can be seen as it (1) begins to pass pulley 170 and (2) about halfway through the passage, respectively. As top rope 22 is moved by drive 18 from end station 30, connection 128 (FIG. 8) approaches pulley assembly 100 of intermediate support station 28. Leading bent end 168 of horizontal cross-piece 164 contacts wire 126 and deflects it to the left as shown and beyond the end of bar 102. The upper portion of wire 126 between cross-piece 164 and flange 178 rides on the upward slope of the outer edge of pulley 170 and passes through gap 180 (FIG. 12) beneath flange 178. Suspension wire 126 is preferably a one-sixteenth inch galvanized metal cable, and tow line 20 is preferably a one-eighth inch galvanized metal cable, so the former will fit through gap 180 while the latter is constrained to remain in pulley 170. Consequently, wire 126 fits loosely in gap 180 whereas tow line 20, and thereby the ferrules 148 and the loosely fitting loop 150 of wire 126, will not fit through. Wire 126 will continue leftward in the drawings, riding on the downward slope of the outer edge of pulley 170 and the outside surface of horizontal cross-piece 164. Note that cross-piece 164 is outside pulley arm 160, to the left in FIG. 11, thereby cross-piece 164 presents a smooth surface to connection wire 126 until the trailing bent end 166 (not seen in FIG. 12) allows wire 126 to return to its non-wedged, merely hanging state. Until past station 28, suspension wire 126 will ride completely on pulley 170 and horizontal cross-piece 164, and it will remain out of contact with all other parts of intermediate support station 28. Inasmuch as this is the sole contact between any part of target retrieval system 10 with the target suspension assembly 124, the movement of target 32 remains free of hindrance.

Each area selected for a home ground of the target retrieval system 10 will be different than any other home ground in length and type of land contours. The length of tow line 20 must be capable of being adjustable, therefore. In order to select the proper length of tow line 20, the hunter setting up target retrieval system 10 decides, after surveying the location, how long target retrieval system 10 will be. The selected distance is doubled, and the cable is measured from a stock drum and cut. FIG. 13 shows the mechanism of joining the free ends together.

Tow line 20 initially has a free end 188, and when the cable is cut to length, it has a second free end 190 joined to free end 188 by a big loop. A short hollow metal tube 192, about one inch long, has free end 188 inserted into one end and free end 190 inserted into the second end. Preferably, free ends 188-190 are essentially abutted, but this is not strictly necessary. After free ends 188-190 are within the hollow metal tube 192, tube 192 is crimped to physically bind the three elements permanently together. Tow line 20 is typically a one-eighth inch galvanized steel cable. A commonly available tube is an ordinary piece of three-sixteenth inch brake line tubing.

There are enormous pressures imposed upon tow line 20 to keep target retrieval system 10 stable and target 32 off the ground 34. A commercially available anchor 78 (FIG. 14) resists those pressures. Anchor 78 has been mentioned previously in FIGS. 3 and 5. Anchor 78 comprises a relatively small U-shaped handle 196, a long, narrow body 198, a pair of auger blades 200, and a tip 202. Handle 196 has two arms 204, and there is a pair of apertures 206 in each of the arms 204 of handle 196. Apertures 206 are sized such as to receive many disparate items (see FIGS. 3 and 5) which may be removably attached to anchor 78.

Anchor 78 is integral and preferably made entirely of steel. Body 198 is approximately thirty inches long and three-quarters of an inch in diameter. Each arm 204 has a substantially rectangular shape of approximately two by three inches, and each aperture 206 is approximately five-sixteenth inches square.

Tip 202 is jammed into ground 34, and an elongated shaft (not shown), such as a dowel or hammer handle, is centrally placed in the bight of handle 196. Rotating the shaft clockwise causes the auger blades 200 to bite into the earth and drive anchor 78 as deep into the earth as desired. The tension-communicating devices, e.g., chain 118, are then attached to the apertures 206 in handle 196 and tension is applied.

Stake 96, another commercially available accessory, is shown in FIG. 15. Stake 96 has been mentioned previously in FIGS. 4 and 5. Legs 94 and 114 of their respective stanchions are reinforced by stakes 96 being driven through them into the ground 34. Stake 96 is essentially a large nail with a shaft 208 and an integral head 210. A cleat 212 encircles shaft 208 and abuts head 210, where cleat 212 is preferably glued to shaft 208. Cleat 212 comprises a pair of diametric arms 214 and 216. An aperture 218 is adjacent the end of arm 214, and a hook 220 is at the end of arm 216. Aperture 218 and hook 220 are designed to be attached to most any connector in the market. For example, guy wires 98 (FIG. 4) are conveniently made of a woven nylon string and are wrapped around the two arms 214 and 216 of cleat 212. A sharp tug on a claw hammer is enough to remove stake 96 from the ground.

It is advantageous for pulley brackets 158 and 120 of intermediate support station 28 and end station 30, respectively, to be adjustable. When the pulley stands 84 and 104 are awkwardly placed, because of the topography, the pulleys 170 and 122 may not receive the top and bottom ropes 22 and 24 smoothly. There could be a certain amount of binding, which is always detrimental. Attaching the pulley brackets by a nut and bolt arrangement solves the problem in many cases. FIGS. 16 and 17 illustrate.

In FIG. 16, bar 102 connects to its stanchion 84 in the normal way. Attached to the end of bar 102 is a pulley bracket 158. Instead of welding bracket 158 to bar 102 in a permanent position, the two are joined by a bolt 222 with an integral head 224 and a nut 226. A wing nut 226 is shown to emphasize the variety of nuts which are suitable for adjustably connecting the two. Any number of washers and locking washers may be used as deemed appropriate. Prior to tightening nut 226, pulley 170 is rotated to align its plane with the direction of tow line 20.

In FIG. 17, pulley 122 is adjustably mounted by attaching bracket 120 to pole 106 of stanchion 104 with a nut and bolt arrangement in the manner of FIG. 16. Because of the angle depicted, only bolt 228 and wing nut 230 are visible. Bolt 228 extends from a head (not shown) within the bight of bracket 120, through aligned apertures in bracket 120 and pole 106, and rearwardly as shown. Pulley 122 can rotate about bolt 228, therefore. A universal connection (not shown) between pole 106 and bracket 120 allows pulley 122 to move essentially independently of base 112 of stanchion 104 and aids in removing all lateral forces from tow line 20. A single, large chain link 232 is welded to pole 106 about three inches from the top thereof. A removable clasp 234 attaches chain 118 (FIG. 5) to chain link 232, when system 10 is assembled.

The materials for stanchions 84 and 104 are specially selected. All of the pipes are square, hollow, one-eighth inch in wall thickness, and made of steel. The pipes are one of two types, interior and exterior, with the only difference between the two being their external dimension. An interior pipe is nominally one inch in outside width, an exterior pipe is nominally one and one-quarter inches in outside width, and an interior pipe telescopically slides within an exterior pipe. Limiting the pipes to two sizes simplifies the manufacture of the retrieval system and the replacement of broken or lost pieces. All that need be done is cut various pipes to length, drill the requisite apertures therethrough, and weld the pieces together. Only two size pipes need be stocked.

Target retrieval system 10 is a large conglomeration. Every effort has been made to make it as compact as possible for storage and transportion. The largest items are the targets and the two stanchions. (Nothing can be done about the targets; they are what they are or they wouldn't be what they are.) FIGS. 18-22 show the preferable embodiments of stanchions 84 and 104.

FIG. 18 shows the details of the top of stanchion 84. Pipe segment 236 is preferably an exterior pipe, approximately two inches long, centered on top of top pole 86, where it is welded. Top pole 86 is an interior pipe, approximately thirty-two inches long, which is telescopically received by bottom pole 88; bottom pole 88 is an exterior pipe and approximately thirty-two inches long. Bar 102 is an interior pipe, approximately thirty-two inches long. A plurality of horizontally aligned openings (not shown) are drilled in both pipe segment 236 and bar 102. A cotter pin 238 through the aligned openings holds bar 102 in place. A chain tether 240 is attached to the cotter pin 238 near one end of pipe segment 236. An inherent benefit to adjusting bar 102 is as one of the adjustments made during setup to overcome unusual topography in order to align the plane of pulley 170 with the direction of tow line 20. An eye bolt 242 is connected to pole 86 by a nut 244, and the previously mentioned guy wires 98 are connected between eye bolt 242 and stakes 96 (FIG. 4).

A compact base of stanchion 84 is shown in FIG. 19. A portion of bottom pole 88 is shown welded to two short pipe segments 246 which form an angle of ninety degrees. Short pipe segments 246 are each exterior pipes and about four inches long. A pair of legs 94 are removably attached to the pair of short pipe segments 246 to support stanchion 84. Each of legs 94 is an interior pipe, about twenty-four inches long, and is telescopically received by each short pipe segment 246. Short pipe segments 246 and legs 94 are held together by cotter pins 248 extending through two pair of horizontal apertures, about three-eighths inch in diameter, in each of said legs and said short pipe segments. A pair of tethers 250 are attached to cotter pins 248 and are welded to bottom pole 88. The free ends of legs 94 include a vertical pair of apertures through which a pair of stakes 96 are driven for stability.

Figure 20:
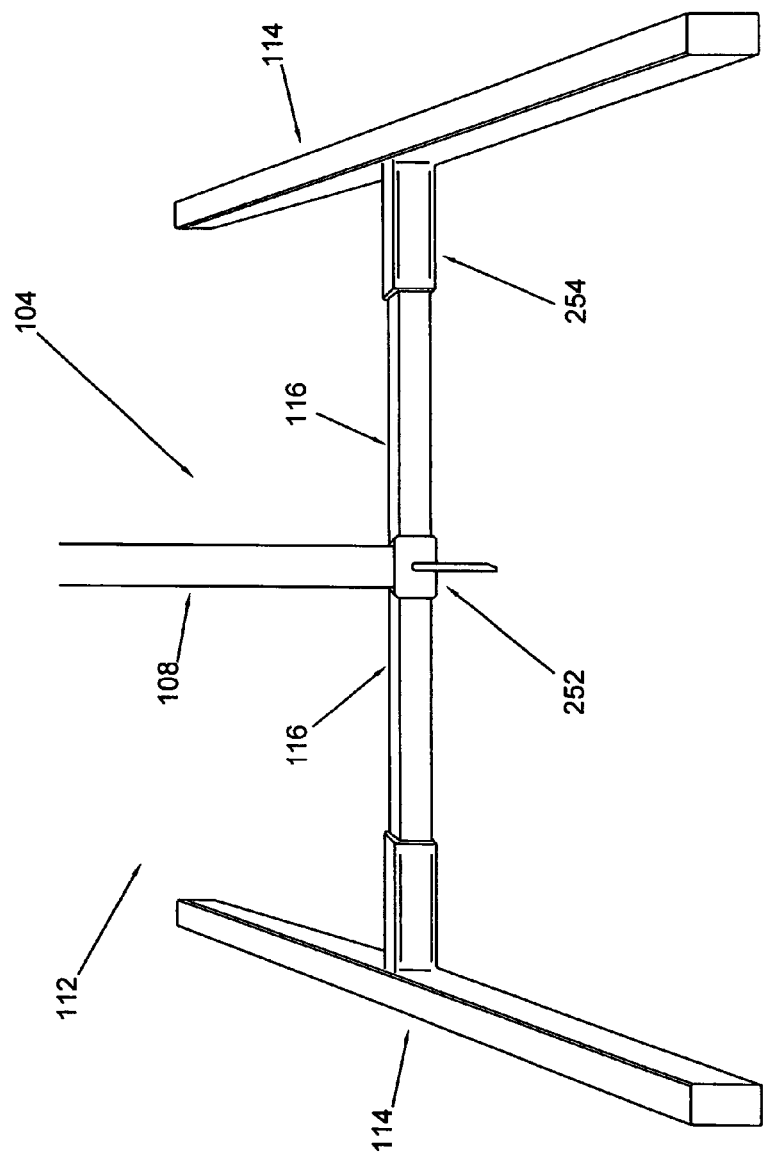
FIG. 20 is a diagrammatic perspective view showing the attachment of the base to the stanchion of the end station.

The intricate base 112 of stanchion 104 is depicted in FIG. 20. Base 112 is comprised of a pair of parallel feet 114 and a cross-foot 116, the latter of which connects bottom pole 108 with feet 114 by means of a joint 252. Another joint 254 allows removably joining foot 116 and parallel feet 114. Both joints 252 and 254 are the subjects of FIGS. 21 and 22, respectively, below.

Figure 21:
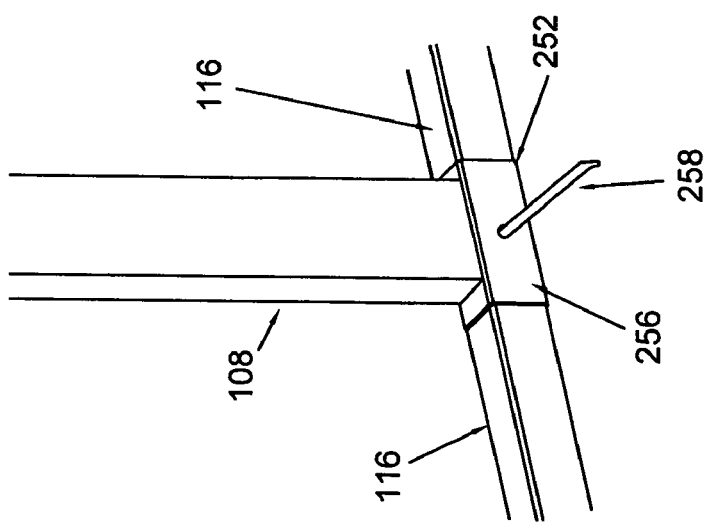
FIG. 21 is a diagrammatic perspective view showing the attachment of the base cross-leg to the stanchion of the end station.

The central joint 252 is shown in FIG. 21. Bottom pole 108 has a short cross-pipe 256 welded to its lower end. Foot 116 telescopes within short cross-pipe 256. A series of three-eighths inch pair of apertures horizontally through foot 116 selectively align with a single pair of like apertures in short cross-pipe 256, and a conventional cotter pin 258 is inserted therethrough to hold the two together. Short cross-pipe 256 is an exterior pipe, about two inches long, and foot 116 is an interior pipe, about twenty-four inches long.

Each of the aforementioned pins are commercially available cotter pins. They each have a circular end and a split pointed end. They are about four and a half inches long, and nominally three-eighths inch in diameter. The cotter pins are secured from loss by welding a chain tether, about fifteen inches long, to an adjacent pipe.

Figure 22:
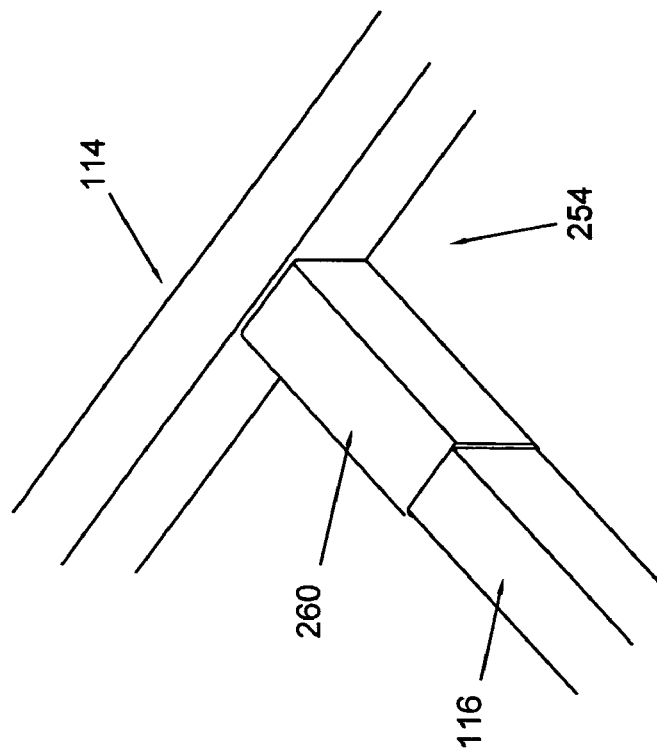
FIG. 22 is a diagrammatic perspective view showing the attachment of the parallel legs of the base of the end station.

Turning to FIG. 22, one of two end joints 254 is shown close-up. Parallel foot 114 has a perpendicular short pipe segment 260 welded to its inside side surface. Short pipe segment 260 is obviously an exterior pipe, inasmuch as cross-foot 116 slides into it when assembled. Foot 114 is preferably also an exterior pipe, since it is easier to handle when welding. It could be an interior pipe, however. Each foot 114 is approximately twenty-four inches long, and short pipe segment 260 is approximately four inches long.

All dimensions are approximate and can be changed at will without warning. They are included only to give the reader a general idea of the approximate size of the elements which make up the target retrieval system.

We claim:

1. A target retrieval system to simulate an indigenous shooting ground, comprising:
   a tree stand, said tree stand built in a tree, said tree stand simulating a hunter's tree stand in a forest from which to shoot at said target, and a ladder provided to reach said tree stand;
   a target;
   a tow line, said tow line defining a path, said target being removably suspended from said tow line, said tow line being tensioned by a manually operated tensioner, and said tow line being supported and guided by two types of stanchions, said two types of stanchions comprising an intermediate stanchion and an end stanchion;
   said intermediate stanchion comprising a pair of legs fixed at substantially a ninety-degree angle, a bottom pole connected to the apex of said pair of legs, a top pole telescopic with said bottom pole, a horizontal bar cantilevered from said top pole, an intermediate pulley attached to one end of said horizontal bar, and a pair of guy wires stabilizing said intermediate stanchion,
   said end stanchion comprising a pair of parallel feet connected by a cross-foot, a bottom pole connected to said cross-foot, a top pole telescopic with said bottom pole, a pulley attached to the top of said top pole, and a chain stabilizing said end stanchion;
   a drive, said drive being located at said shooter's area, said drive being attached to said tow line to move said tow line, and said drive being intermittently controlled to move said target to a selected location along said path; and
   said target retrieval system being capable of being alternately installed and dismantled in a selected environment.

2. The target retrieval system of claim 1, wherein said stanchions are reinforced by locking them to the earth with stakes.

3. The target retrieval system of claim 1, wherein said selected environment having topography which is uneven, wherein each of said support pulleys being adjustable relative to said stanchion, and wherein said stanchions are optimally located and said pulleys are adjusted to accommodate said environment.

4. The target retrieval system of claim 1, wherein said shooter's area comprises a deck, and the selected environment comprises a back yard.

5. A target retrieval system for an archer's practice shooting, comprising:
   a conveyor comprising a closed loop having two essentially U-shaped ends and two lines between said two ends, said two lines being adjacent one another along their entire lengths, and said two lines simultaneously traveling in opposite directions when said closed loop is moving;
   a target, said target being carried by one of said two lines;

a drive station supporting one end of said conveyor;
at least one intermediate station, said intermediate station being positioned between said drive station and said end station, said intermediate station comprising a portable support, said portable support comprising a plurality of pieces comprising a removable base, an adjustable pole extending upwardly from said base, an adjustable cross-bar cantilevered horizontally from said adjustable pole, and an intermediate pulley attached to said cross-bar, said intermediate pulley supporting said two lines of said closed loop;
an end station supporting the other end of said conveyor, said end station comprises a portable stanchion, said portable stanchion comprising a base, an adjustable pole extending upwardly from said base, a cross-bar cantilevered from said adjustable pole, and an end pulley attached to said cross-bar, and a guy wire being connected between said adjustable pole and an anchor embedded into the earth, said guy wire resisting the tensions imposed on said end pulley by said conveyor;
both of said two lines following substantially the same pathway between said drive station and said end station;
a tension adjusting station between said drive station and said end station, a tensioner, said conveyor being tensioned by said tensioner; and
said drive station including a drive, said drive being intermittently controlled to move said line, said drive thereby selectively moving said target to a specific location along said line for use and to said drive station for retrieval of said target and thereby the arrows embedded in said target without the archer needing to leave the drive station.

6. The target retrieval system of claim 5 wherein said removable base of said intermediate station comprises a pair of feet, said pair of feet subtending substantially ninety degrees, and the apex of said pair of feet is removably attached to said pole, said pair of feet underlying said intermediate pulley, and each of said feet being secured to the ground by a stake.

7. The target retrieval system of claim 5 wherein said target is carried on one of said two lines by a suspension connected to both said one of said two lines and said target, and said intermediate pulley includes two guards, one of said guards being positioned on one side of said pulley and has a portion which overlaps both the front and back of said pulley to allow said suspension to pass said intermediate pulley without fouling, and the other of said guards being positioned on the other side of said pulley and has a portion which overlaps the top of said pulley to prevent any line from rising out of said pulley.

8. The target retrieval system of claim 5 wherein both of said stanchions for said end station and for said intermediate station comprise a plurality of hollow pipes having two different cross-sectional dimensions such that one pipe telescopically slides within the other pipe, and wherein said plurality of hollow pipes provide for assembly and disassembly of said stanchions.

9. A target retrieval system for an archer's practice shooting, comprising:
a conveyor comprising a closed loop having two essentially U-shaped ends and two lines between said two ends, said two lines being adjacent one another along their entire lengths, and said two lines simultaneously traveling in opposite directions when said closed loop is moving;
a target, said target being carried by one of said two lines;
a drive station supporting one end of said conveyor, said drive station further comprises a bracket removably affixed at said drive station, a drive pulley journaled on said bracket, said drive pulley supporting and guiding both of said two lines of said conveyor, and said drive attached to said drive pulley for operating said drive pulley, and said drive station comprises a portable stanchion, said portable stanchion comprising a base, an adjustable pole attached to and extending upwardly from said base, a cross-bar cantilevered from said pole, a bracket attached to said cross-bar, and said drive pulley journaled on said bracket; said base comprising a pair of feet and a cross-foot, said pair of feet comprising a foot removably attached to each end of said cross-foot, said cross-foot being adjustably connected to said pole, said cross-foot holding said pair of feet apart substantially parallel to each other; and a guy wire being connected between said adjustable pole and an anchor embedded into the earth, said guy wire resisting the tensions imposed on said drive pulley by said conveyor, and said drive station portable stanchion being additionally reinforced against tension by locking said pair of parallel feet to the earth with stakes;
an end station supporting the other end of said conveyor;
both of said two lines following substantially the same pathway between said drive station and said end station;
a tension adjusting station between said drive station and said end station, a tensioner, said conveyor being tensioned by said tensioner; and
said drive station including a drive, said drive being intermittently controlled to move said line, said drive thereby selectively moving said target to a specific location along said line for use and to said drive station for retrieval of said target and thereby the arrows embedded in said target without the archer needing to leave the drive station.

10. A target retrieval system for an archer's practice shooting, comprising:
a conveyor comprising a closed loop having two essentially U-shaped ends and two lines between said two ends, said two lines being adjacent one another along their entire lengths, and said two lines simultaneously traveling in opposite directions when said closed loop is moving;
a target, said target being carried by one of said two lines;
a drive station supporting one end of said conveyor;
an end station supporting the other end of said conveyor;
both of said two lines following substantially the same pathway between said drive station and said end station;
a tension adjusting station between said drive station and said end station, a tensioner, said conveyor being tensioned by said tensioner, said tension adjusting station comprises a double-sheave pulley supporting said two lines and an anchor placed in the ground, and a tensioner, said tensioner being manually operated and said tensioner being connected between said double-sheave pulley and said anchor, and said tensioner selectively adjusting the tension between said double-sheave pulley and said anchor, whereby said closed loop is simultaneously tensioned; and
said drive station including a drive, said drive being intermittently controlled to move said line, said drive thereby selectively moving said target to a specific location along said line for use and to said drive station for retrieval of said target and thereby the arrows embedded in said target without the archer needing to leave the drive station.

11. A target retrieval system for an archer's practice shooting, comprising:
a conveyor comprising a closed loop having two essentially U-shaped ends and two lines between said two ends, said two lines being adjacent one another along their entire lengths, and said two lines simultaneously traveling in opposite directions when said closed loop is moving;

a target, said target being carried by one of said two lines;

a drive station supporting one end of said conveyor;

an end station supporting the other end of said conveyor, said end station comprises a portable stanchion, said portable stanchion comprising a base, said base of said end station comprises a cross-foot adjustably attached to said adjustable pole, and a pair of feet, said feet comprising a foot removably attached to each end of said cross-foot, said cross-foot holding said pair of feet apart substantially parallel to each other, an adjustable pole extending upwardly from said base, a cross-bar cantilevered from said adjustable pole, and an end pulley attached to said cross-bar, and a guy wire being connected between said adjustable pole and an anchor embedded into the earth, said guy wire resisting the tensions imposed on said end pulley by said conveyor;

both of said two lines following substantially the same pathway between said drive station and said end station;

a tension adjusting station between said drive station and said end station, a tensioner, said conveyor being tensioned by said tensioner; and said drive station including a drive, said drive being intermittently controlled to move said line, said drive thereby selectively moving said target to a specific location along said line for use and to said drive station for retrieval of said target and thereby the arrows embedded in said target without the archer needing to leave the drive station.

* * * * *